(12) United States Patent
Zlotnik et al.

(10) Patent No.: US 9,596,848 B2
(45) Date of Patent: Mar. 21, 2017

(54) FORMULATIONS AND USES OF DIPHENYL

(71) Applicant: Ideaz, LLC, Pittsburgh, PA (US)

(72) Inventors: Cliff Zlotnik, Sewickley, PA (US); Harry Velgich, Canonsburg, PA (US)

(73) Assignee: Ideaz, LLC, Pittsburgh, PA (US)

( * ) Notice: Subject to any disclaimer, the term of this patent is extended or adjusted under 35 U.S.C. 154(b) by 127 days.

(21) Appl. No.: 14/579,370

(22) Filed: Dec. 22, 2014

(65) Prior Publication Data

US 2015/0173353 A1 Jun. 25, 2015

Related U.S. Application Data

(60) Provisional application No. 61/919,022, filed on Dec. 20, 2013, provisional application No. 62/090,075, filed on Dec. 10, 2014.

(51) Int. Cl.
| | | |
|---|---|---|
| *A01N 25/16* | (2006.01) | |
| *A01N 27/00* | (2006.01) | |
| *A61L 9/012* | (2006.01) | |
| *A61L 9/04* | (2006.01) | |

(52) U.S. Cl.
CPC .............. *A01N 27/00* (2013.01); *A61L 9/042* (2013.01); *A61L 2209/21* (2013.01)

(58) Field of Classification Search
CPC ........ A01N 31/08; A01N 33/12; A01N 65/22; A61L 2209/21
See application file for complete search history.

(56) References Cited

U.S. PATENT DOCUMENTS

| | | | |
|---|---|---|---|
| 2,897,111 A | | 7/1959 | Lloyd et al. |
| 3,284,275 A | * | 11/1966 | Nelson ................... C08J 9/0014 264/321 |
| 3,413,218 A | | 11/1968 | Einsel et al. |
| 3,876,762 A | * | 4/1975 | Rabussier ........... A01M 1/2044 239/60 |
| 4,117,110 A | | 9/1978 | Hautmann |
| 5,034,222 A | | 7/1991 | Kellett et al. |
| 2007/0081957 A1 | | 4/2007 | Taguchi et al. |
| 2011/0189464 A1 | * | 8/2011 | Steinke ..................... B32B 5/16 428/304.4 |
| 2012/0324661 A1 | | 12/2012 | Dedominicis et al. |

OTHER PUBLICATIONS

Search Report and Written Opinion dated Apr. 1, 2015, for corresponding International Patent Application No. PCT/US2014/071936.

* cited by examiner

*Primary Examiner* — Alma Pipic
(74) *Attorney, Agent, or Firm* — Beck & Thomas, P.C.

(57) ABSTRACT

The present disclosure provides diphenyl-impregnated compositions that are capable of delivering diphenyl into an environment for extended periods of time. In some embodiments, the compositions include a melamine copolymer foam, with formaldehyde-melamine-sodium bisulfite copolymer foams being particular effective. The present disclosure also provides methods for the manufacture of diphenyl-impregnated compositions and methods of using those compositions to achieve effective odor and mold/other fungi control.

13 Claims, 2 Drawing Sheets

FORMULATIONS AND USES OF DIPHENYL

CROSS-REFERENCE TO RELATED APPLICATIONS

This application claims the benefit under 35 U.S.C. §119 (e) of the earlier filing date of U.S. Provisional Patent Applications Nos. 61/919,022 filed on Dec. 20, 2013 and 62/090,075 filed on Dec. 10, 2014.

BACKGROUND OF THE INVENTION

1. Field of the Invention

The present invention relates generally to the field of fungal and odor control, and more specifically to providing a material that creates a uniform and continuous release of diphenyl vapor such that the emitted vapor effectively reduces malodors and the growth of fungi for an extended period of time.

2. Description of the Background

Diphenyl is an organic compound that has a variety of applications. Diphenyl's chemical structure is shown below:

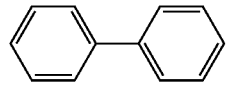

Diphenyl is commonly manufactured in the form of a powder or flake. The powder/flake diphenyl is problematic to work with in that it is messy and is difficult to keep in one place. Thus, loose diphenyl granules or flakes are considered undesirable and may be considered a contaminant. However, diphenyl has a melting point of 70° C., permitting it to be melted to a liquid easily. The liquid is more easily handled than flake or powder diphenyl.

One application of diphenyl is in the prevention of mold and fungus growth. Diphenyl has been used as a preservative, particularly by impregnation of papers used in the transport of citrus fruits with diphenyl. Those papers could then be used to wrap the fruit, retarding mold and fungus growth. U.S. Pat. Nos. 2,173,453 and 2,746,872 (hereby incorporated by reference) disclose the preparation and use of such diphenyl-impregnated papers for this purpose. Currently, the primary uses for diphenyl are as a component in heat transfer fluids and in dyeing fabrics.

In addition to its anti-mold and anti-fungal properties, diphenyl also has a pleasant smell and odor counteractant properties and may also be used as a deodorizer. Indeed, there are many applications where both properties—a deodorizer and an anti-fungal/mold—may be desirable. Such instances may include putting diphenyl-containing products around areas of the home prone to water damage (e.g., basements, boats, closets, bathrooms) or for use in disaster area clean-up, particularly in areas affected by rain and/or flooding, to prevent both fungal growth as well as the odors associated with moisture/fungal growth. Diphenyl-containing materials may also be used as a deodorizing agent in hotels, bathrooms, kitchens, homes with pets, vehicles, and in smoking areas. Diphenyl is not readily water soluble, thus, may be useful as deodorizer or fungistat in drains or other areas where the product may come into regular contact with water.

Despite the wide ranging benefits of diphenyl, its use remains somewhat limited and primarily restricted to citrus fruit transportation. While diphenyl-impregnated paper is effective for wrapping fruit, delivery of diphenyl from paper is relatively rapid, thus exhausting the source of diphenyl quickly. That attribute renders such formulations ineffective in domains where longer delivery times of diphenyl are desired.

Two commercially available products using diphenyl for odor control are the Damp Check Magic Disk and Sun-Fresh Crystal Disk. The Crystal Disk is molded or cast, again, onto a paper substrate wherein the paper is a barrier to air movement. The product label states that the Crystal Disk is "often used in vacuum cleaners." The paper substrate is fragile, flimsy, and lacks mechanisms of attachment suitable to fix the product at a particular location. Users are directed to place the device in return air locations, rather than supply airstream conduits.

There remains a need for a versatile and durable material that can serve as a vehicle for delivery of deodorizing, anti-fungal diphenyl. Here, we disclose a solid material impregnated with diphenyl that provides uniform and sustained release of diphenyl over an extended period of time. The solid material is easily impregnated with diphenyl, is structurally sound, can be manufactured into a variety of shapes and sizes, and is fire and heat resistant. The material has the capacity to release diphenyl over the course of 1-2 months, or longer, depending on the air flow and temperature of the environment in which it is placed.

SUMMARY OF THE INVENTION

The present invention provides compositions of diphenyl and methods of manufacture thereof. The compositions provide for the extended and efficient release of diphenyl. In some embodiments, the compositions include employ a foam to provide the base of the composition. In some embodiments, the foam is a polymer. In certain embodiments, the foam is a melamine copolymer foam, and in some instances, the foam is a formaldehyde-melamine-sodium bisulfite copolymer foam.

Liquid, melted diphenyl may be used to impregnate the foam. It has been found that briefly dipping the foam composition into molten diphenyl causes rapid uptake of the diphenyl into the foam. The foam composition may then be removed from the molten diphenyl and allowed to dry. The resulting composition includes solid diphenyl that may later sublime, thus permitting delivery into an environment to achieve odor control and to limit the growth of mold and other fungi. The compositions may be formed in any shape appropriate for the specific implementation confronting the practitioner. The compositions may be additionally impregnated with other components, such as fragrance, paraffin, colorant, or dye, to achieve desired aesthetic attributes for the composition.

DESCRIPTION OF THE DRAWINGS

Further aspects of the present disclosure together with additional features contributing thereto and advantages accruing there from will be apparent from the following description of embodiments of the disclosure which are shown in the accompanying figures wherein.

DETAILED DESCRIPTION OF THE INVENTION

Figure 1:
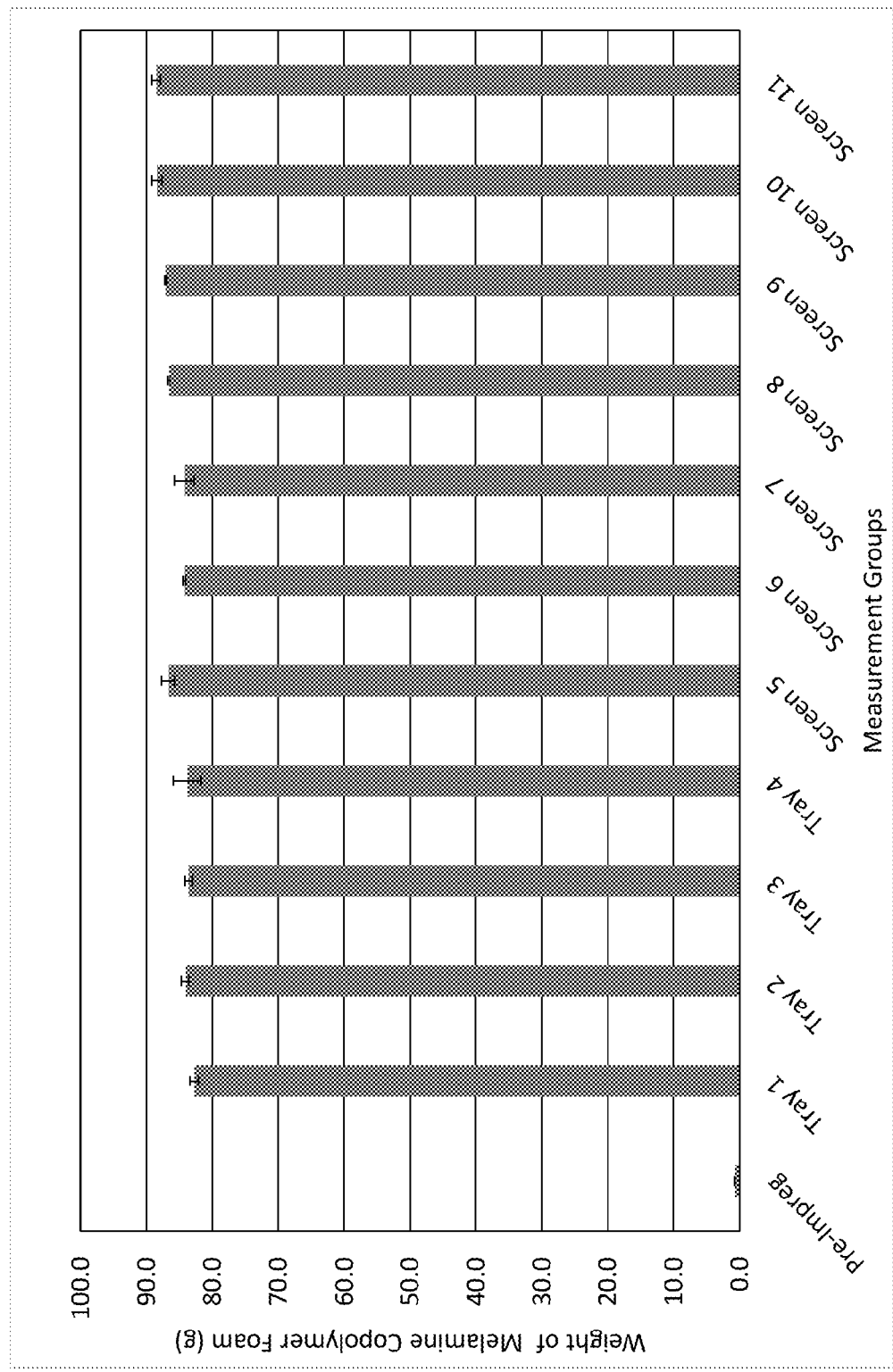
FIG. 1 is a bar graph showing the increase in weight between the pre-impregnated foam and diphenyl-impregnated foam from eleven different batches or groups of diphenyl-impregnated foam.

It is to be understood that the figures and descriptions of the present invention have been simplified to illustrate elements that are relevant for a clear understanding of the invention, while eliminating for purposes of clarity, other elements that may be well known. The detailed description will be provided herein below with reference to the attached drawing.

The present invention provides solid formulations containing diphenyl that may achieve sustained-release of diphenyl. In some embodiments, the solid formulations containing diphenyl permit delivery of diphenyl (typically in vapor form) over the course of weeks and, in some embodiments, for months. The present invention also provides methods for the impregnation of a solid with diphenyl. The solid formulations containing diphenyl may be used in a diversity of settings to achieve such benefits as fungal and mold growth inhibition, odor control, and scent delivery for extended periods of time.

Another aspect of the present invention provides methods for controlling fungal and mold growth using a material impregnated with diphenyl, such that diphenyl is released from said material to impart anti-fungal/-mold effects for an extended period of time.

Liquid diphenyl may be used to impregnate a variety of materials, including woven and non-woven textiles, felts, cellulose, and sponge-like materials. In some particularly useful embodiments of the present invention, the material impregnated with diphenyl is a sponge-like material. It has been found that melamine copolymer foam is particularly effective at being loaded with liquid diphenyl. In some embodiments, the melamine foam may be a formaldehyde-melamine-sodium bisulfite copolymer. Diphenyl may be loaded as a liquid into the melamine copolymer foam. The diphenyl-impregnated melamine copolymer foam may then be allowed to air dry, resulting in a solid formulation.

In such embodiments, impregnation of the foam with diphenyl may result in a hard, seemingly crystalline material. That formulation may be manipulated in numerous ways to increase its utility in diverse household and industrial applications. For example, the diphenyl-impregnated melamine copolymer foam may be cut into shapes appropriate for specific applications or may have holes drilled into it, allowing it to be secured to particular locations. In certain embodiments, impregnated diphenyl compositions may be secured in a desired location by hooks, straps, grommets, bungee cords, nails, screws, Velcro, etc. One of skill in the art will recognize many additional mechanisms by which diphenyl-impregnated melamine copolymer foam may be secured in a particular location. Additionally, the diphenyl-impregnated foam may include holes that permit air flow through the composition, thus promoting delivery of diphenyl to the environment.

Within the context of the present invention, diphenyl-impregnated compositions may be fabricated as an integrated part of another device. For example, a piece of diphenyl-impregnated foam may be formed and/or cut to be placed over the rotor of a fan to promote delivery of diphenyl to the environment. As another example, the diphenyl-impregnated foam may be formed and/or cut to take the shape of an ornamental element of an apparatus. The diphenyl-impregnated foam may further be colored to add decorative appeal to the component. As an example of this implementation, a piece of diphenyl-impregnated foam may be formed and/or cut to take the form of a decorative grate which may be placed in front of an air vent to permit efficient and effective delivery of diphenyl to an environment. One of ordinary skill in the art will recognize myriad implementations of the present invention in this context, limited only by the circumstances in which the implementation occurs.

It has been found that diphenyl sublimes and escapes from the impregnated copolymer foam, providing a mechanism for extended delivery of diphenyl vapor. Following substantially complete sublimation of the diphenyl, the foam commonly returns to its original soft and pliable form. In some embodiments, the foam may be re-impregnated with diphenyl and reused.

In some embodiments where the material is melamine copolymer foam, it has been found that a foam thickness of less than about 0.5 inches is particularly useful for effective and substantially uniform impregnation of the material with diphenyl. In some embodiments, the following methods are employed to impregnate melamine copolymer foam. Solid diphenyl is heated to a temperature greater than its melting temperature (70° C.) to form molten diphenyl. In some embodiments, molten diphenyl is held at approximately 75° Celsius. A plurality of pieces of melamine copolymer foam is placed onto a solid perforated horizontal surface which is submerged into the molten diphenyl for a period of time, thus exposing the pieces of melamine copolymer foam to the molten diphenyl. In some embodiments, the perforated horizontal surface is a screen or a tray. It has been found that a reduced solid surface area of a perforated horizontal surface increases effective incorporation of diphenyl into the melamine copolymer foam. It has also been found that exposure times of approximately 10-15 seconds are particularly effective at consistently and efficiently impregnating melamine copolymer foam with diphenyl.

Following impregnation, the perforated horizontal surface and pieces of melamine copolymer foam are removed from the molten diphenyl by lifting the screens that hold the pieces of melamine copolymer foam vertically out of the molten diphenyl, such that the screens remain parallel to the surface of the molten diphenyl. Once removed from the molten diphenyl, the screens and foam pieces are held stationary in the same orientation, with the screens parallel to the surface of the molten diphenyl, for about 10-15 seconds. The screens are then placed in a secure location to permit the diphenyl-impregnated melamine copolymer foam to dry. The dried and impregnated melamine copolymer foam adopts a solid form, which may include what appear to be crystalline formations of solid diphenyl. This method may be used to consistently and uniformly impregnate numerous pieces of melamine copolymer foam. Table 1 below provides data demonstrating the consistent impregnation achieved by these methods. Sixteen pieces of melamine copolymer foam were chosen at random and weighed prior to impregnation (column labeled 'Pre-impreg Weight (g)'). All pieces were then impregnated with molten diphenyl. After impregnation, the impregnated copolymer foam pieces were weighed. The same data presented in Table 1 are presented in graphical form in FIG. 1. In some implementations, these techniques may be used to impregnate the melamine copolymer foam with over 100× its weight in diphenyl.

TABLE 1

Loading of pieces of melamine copolymer foam.

| Pre-impreg Weight (g) | Tray 1 | Tray 2 | Tray 3 | Tray 4 | Screen 5 | Screen 6 | Screen 7 | Screen 8 | Screen 9 | Screen 10 | Screen 11 |
|---|---|---|---|---|---|---|---|---|---|---|---|
| 0.9 | 84 | 83.1 | 84.4 | 94 | 87 | 84.1 | 79.6 | 87.1 | 87.1 | 88.4 | 89.5 |
| 0.7 | 78.1 | 82.6 | 83.7 | 94.1 | 87 | 85.3 | 87.8 | 87.2 | 87.9 | 93.3 | 90 |
| 0.7 | 83.2 | 84.8 | 83.2 | 84.6 | 86 | 84 | 85 | 86.3 | 87.9 | 88.2 | 88.7 |
| 0.7 | 84 | 82.9 | 79.1 | 82.4 | 86.9 | 84 | 84.3 | 86.6 | 87.2 | 83.7 | 89.2 |
| 0.7 | 83.3 | 80.9 | 84.2 | 83.3 | 90.3 | 85 | 85.4 | 87 | 86.5 | 88.6 | 83 |
| 0.7 | 84.1 | 84.4 | 86.6 | 83.5 | 91 | 84.2 | 92.5 | 85.8 | 86.7 | 87.6 | 89.9 |
| 0.7 | 84.8 | 83.9 | 83.7 | 79.1 | 86.7 | 83.9 | 75.2 | 87 | 87 | 88.1 | 87.9 |
| 0.7 | 81 | 86 | 83.1 | 83.7 | 86.5 | 83.6 | 84.2 | 86.3 | 86.8 | 87.9 | 87.8 |
| 0.8 | 81.6 | 87.5 | 84.4 | 81.8 | 86.8 | 84.4 | 84 | 86.2 | 87 | 89.3 | 89.3 |
| 0.8 | 83 | 84.8 | 83.2 | 71.5 | 79 | 84.2 | 84.2 | 86.9 | 86.9 | 88.9 | 89.8 |

In some embodiments, the material may additionally be impregnated with fragrance. It has been found that diphenyl may be used as a vehicle to effectively impregnate a piece of foam (e.g., a melamine copolymer foam) with fragrance. In some embodiments of the present invention, the diphenyl- and fragrance-impregnated foam may be used to delivery both diphenyl and fragrance over an extended period of time. Particularly effective fragrances include oil-based fragrances used in candle manufacture. In yet more embodiments, dyes, colorants, or other additives may be added to the diphenyl to impart color to finished products. Such dyes or colorants may be coordinated with the fragrance to produce an aesthetically pleasing article. In general, any additive that is miscible in molten diphenyl may be useful within the context of the present invention.

In some embodiments, the diphenyl may be dissolved in a solvent before impregnation. For example, organic solvents such as ethers, alcohols, or mixtures thereof may be used to dilute the amount of diphenyl impregnated into the melamine copolymer foam. In other embodiments, the melamine copolymer foam may be impregnated additionally with paraffin wax, soy wax, palm wax, and other waxes. These additional components may dilute the diphenyl to lower cost of formulation, modify the sublimation properties of the diphenyl, or adjust the safety of the product by decreasing diphenyl levels within the product.

In additional embodiments, the diphenyl-impregnated material may be combined with desiccants, for example, silica gel, which may provide an additional level of fungistatic action and continue to provide protection after the desiccant has maximized water absorption.

In other embodiments, the diphenyl-impregnated material may be combined with antimicrobials of similar or different chemical classes, for example, o-polyphenol, thymol, thyme oil, and quaternary ammonium chlorides, to achieve synergistic antimicrobial efficacy.

Within the context of the present invention, the delivery of diphenyl from the impregnated melamine copolymer foam may occur by sublimation. To assess delivery of diphenyl, melamine copolymer foam pieces were impregnated with both diphenyl and 1.5% fragrance and were placed in adjacent bathrooms. In one example, the impregnated melamine copolymer foam was incorporated into a small battery-operated fan air freshener device which ran continuously (148 hours per week). In another example, the impregnated melamine copolymer foam was placed in a bathroom without the fan air freshener device, but rather simply left open to the environment. The change in mass of the diphenyl-impregnated melamine copolymer foam over time after placement within the bathroom was measured, as an indicator of the product lifetime and delivery of diphenyl.

Figure 2:
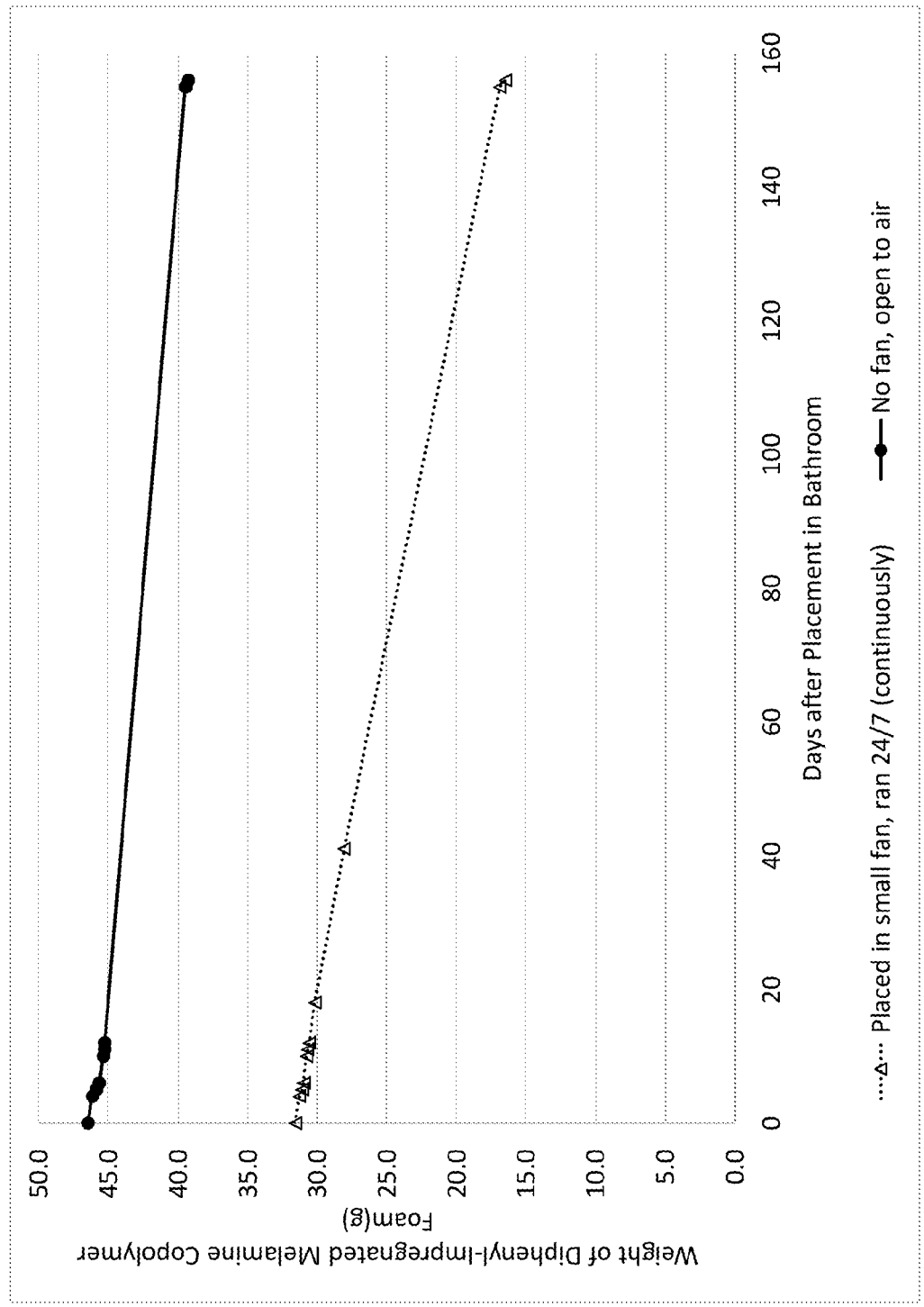
FIG. 2 illustrates the decrease in weight from diphenyl release from diphenyl-impregnated foam over time when placed in bathrooms, wherein the melamine was either placed within a battery-operated fan air freshener device run continuously or wherein the melamine was simply placed in a location that is open to the environment.

In these two examples, uniform delivery of diphenyl was achieved for periods up to five months. The pieces of diphenyl-impregnated melamine copolymer foam appeared to still retain diphenyl at the end of this period, so further delivery of diphenyl beyond the five-month period is expected. The mass of the pieces of diphenyl-impregnated melamine copolymer foam over time are presented in Table 2 and graphically in FIG. 2. As shown, the diphenyl-impregnated melamine copolymer foam consistently deliver diphenyl into the environment for at least five months after initial placement. As expected, the diphenyl-impregnated melamine copolymer foam placed in a continuously running fan air freshener device delivered more diphenyl over the five months (due to active transport of the diphenyl) than the diphenyl-impregnated melamine copolymer foam simply placed in the bathroom without the fan device. These data suggest a functional product life span that may exceed six months for pieces of diphenyl-impregnated melamine copolymer foam.

TABLE 2

Delivery of diphenyl from diphenyl-impregnated melamine copolymer foam.

| Date | Day | Fan air freshener device, run continuously | No fan/device |
|---|---|---|---|
| 27-Jun | 0 | 31.6 | 46.5 |
| 01-Jul | 4 | 31.3 | 46.2 |
| 02-Jul | 5 | 31.1 | 45.9 |
| 03-Jul | 6 | 31 | 45.7 |
| 07-Jul | 10 | 30.8 | 45.4 |
| 08-Jul | 11 | 30.7 | 45.3 |
| 09-Jul | 12 | 30.6 | 45.3 |
| 15-Jul | 18 | 30.2 | |
| 07-Aug | 41 | 28.1 | |
| 29-Nov | 155 | 16.9 | 39.5 |
| 30-Nov | 156 | 16.5 | 39.3 |

Nothing in the above description is meant to limit the present invention to any specific materials, geometry, or orientation of elements. Many modifications are contemplated within the scope of the present invention and will be apparent to those skilled in the art. The embodiments described herein were presented by way of example only and should not be used to limit the scope of the invention.

The invention claimed is:

1. A composition useful for the delivery of diphenyl into an environment, comprising a melamine copolymer foam impregnated with diphenyl, wherein the melamine copolymer foam comprises formaldehyde-melamine-sodium bisulfate copolymer.

2. The composition of claim 1, where the composition further includes an additive selected from the group consisting of antimicrobial, fragrance, paraffin, colorant, and dye.

3. The composition of claim 2, where the antimicrobial is selected from the group consisting of o-polyphenol, thymol, thyme oil, and quaternary ammonium chloride.

4. A method for preparing a diphenyl-impregnated foam, comprising the steps of:
    placing a piece of melamine copolymer foam onto a perforated horizontal surface, wherein the melamine copolymer foam comprises formaldehyde-melamine-sodium bisulfite copolymer;
    dipping the piece of melamine copolymer foam and perforated horizontal surface into a volume of molten diphenyl;
    removing the piece of melamine copolymer foam and perforated horizontal surface from the molten diphenyl; and
    drying the piece of melamine copolymer foam.

5. The method of claim 4, where the dipping step is about 10 to about 15 seconds.

6. The method of claim 4, where the perforated horizontal surface is a screen or a tray containing holes.

7. The method of claim 4, where the molten diphenyl is held at about 75° C.

8. A method of delivering diphenyl to an environment, comprising placing a diphenyl-impregnated composition comprising melamine copolymer foam impregnated with diphenyl in the environment, wherein the melamine copolymer foam comprises formaldehyde-melamine-sodium bisulfite copolymer, and where the diphenyl-impregnated composition delivers diphenyl into the environment.

9. The method of claim 8, where diphenyl is delivered through sublimation.

10. The method of claim 8, where delivery of diphenyl occurs through passive sublimation.

11. The method of claim 8, where delivery of diphenyl occurs through active transport of diphenyl away from the diphenyl-impregnated composition.

12. The method of claim 11, where the active transport of diphenyl is achieved by forcing air to flow over the diphenyl-impregnated composition.

13. The method of claim 8, where diphenyl is delivered into the environment from the diphenyl-impregnated composition for a period of at least three months.

* * * * *